United States Patent [19]

Catalano

[11] Patent Number: 4,579,116

[45] Date of Patent: Apr. 1, 1986

[54] OCULAR MUSCLE HOOK

[76] Inventor: J. Denis Catalano, 609 Claymont Estates Dr., Ballwin, Mo. 63011

[21] Appl. No.: 660,632

[22] Filed: Oct. 15, 1984

[51] Int. Cl.[4] ............................................. F24C 15/20
[52] U.S. Cl. ................................................. 128/303 R
[58] Field of Search .................... 128/303 R, 341, 304, 128/361, 323, 352, 20

[56] References Cited

U.S. PATENT DOCUMENTS 2,117,312  5/1938  Gauly .............................. 128/303 R

FOREIGN PATENT DOCUMENTS 3225620  2/1983  Fed. Rep. of Germany ... 128/303 R
724486   1/1932  France ............................. 128/303 R
158573   1/1920  United Kingdom ............. 128/303 R

*Primary Examiner*—Jay N. Eskovitz
*Attorney, Agent, or Firm*—Haverstock, Garrett & Roberts

[57] ABSTRACT

An ocular muscle hook used in ocular surgery having a muscle holding tip and a handle, a shank extending forwardly of the handle, a leg extending from the forward end of the shank, a tip connected to the forward end of the leg. The leg and the tip define an angle of approximately 150°. The leg and the shank define an angle of approximately 120°, thereby positioning the hand of an individual holding the muscle hook laterally away from interference with the line of sight of the surgeon. When the leg is pulling an eye muscle away from an eye, the upwardly angled tip acts as a stop to prevent the muscle from sliding off the leg. The handle is substantially cylindrical in shape and is sized to be held between the thumb and fingers of a hand providing maximum control, comfort, and familiarity to the individual using the muscle hook.

7 Claims, 5 Drawing Figures

OCULAR MUSCLE HOOK

BACKGROUND OF THE INVENTION

This invention relates to a muscle hook that is particularly useful in ocular surgery, primarily to hold an eye muscle during surgery that is being performed to correct a strabismus condition. Surgery to correct strabismus usually involves shortening or lengthening of one or more of the eye muscles. To do this surgery, the eye muscle must first be cut away from the schlera of the eyeball so that it can be reattached at a different location on the eyeball. The surgeon's object is to make the cut flush with the surface of the schlera. In preparation for this cut, the primary function of the ocular muscle hook is to lift the muscle away from the eyeball to expose the end of the muscle at its place of attachment to the eyeball.

A major problem with muscle hooks of the prior art is that their design requires the hand of the surgeon (or of an assistant) that is holding the muscle hook to be positioned in interference with or obstruction of the surgeon's view of the operating area. The configuration of the present ocular muscle hook is such that, while the hook is in the actual application of holding an eye muscle, the hand holding the muscle hook is positioned laterally away from the surgeon's direct visual line to the operating area.

As a preliminary to the cutting of an eye muscle, the muscle must be identified. The muscle hook of the present invention has a tip on its leading end. The tip is shaped like a bulbous disk with all surfaces and edges rounded. The tip can be used as a probe to locate and identify the muscle to be cut and in so doing, the rounded surfaces and edges avoid cutting or tearing of the schlera. Also, once the muscle has been identified, to lift it, the muscle hook must be pushed beneath the eye muscle between the muscle and the schlera. In this procedure, the tip acts somewhat as a plow leading the way. Because of the width of the tip and because of its rounded faces and edges, tearing of the schlera is avoided as this plowing takes place.

Another problem with muscle hooks of the prior art is that they are awkward to hold and to manipulate. The muscle hook of this invention has a cylindrical handle of size, shape and weight similar to those of a mechanical pencil. The muscle hook is comfortable to hold and easy to manipulate. The cylindrical handle can be held within the thumb and first and second fingers of a hand, can be easily rotated, and can be tilted. The length of the handle is such that its upper end can rest against the body of the hand to provide stability during use of the muscle hook.

In use the muscle hook must be carefully and precisely manipulated as it is moved through the various angular paths. Initially, the thumb and fingers may simultaneously tilt and rotate the handle as the tip of muscle hook probes to identify the eye muscle to be lifted. Next a pivoting and shoving hand motion will be required to cause the tip to plow between the eye muscle and schlera. Once the tip has cleared the other side of the eye muscle, the muscle hook will be pivoted to align the leg of the muscle hook and under the eye muscle. Finally, the muscle hook will be lifted to raise the eye muscle from the eyeball. These various complex maneuvering motions are greatly facilitated by the shape of the handle combined with the angular relationship between the handle leg and tip of this muscle hook.

Another feature of this invention is the provision of a family of surgical instruments, of which this muscle hook is one, such that the size and shape of the handle and the overall weight of the muscle hook are all similar to those of other surgical instruments of the family. Thus, each instrument feels and handles much the same as the others and all are comfortable and familiar-feeling to the surgeon.

An important object of this invention is to provide an ocular muscle hook having a handle and a muscle holding leg projecting angularly from the handle to position a hand holding the handle away from the surgeon's line of vision when the leg is raising an eye muscle. Another object is to provide such a muscle hook with a tip angled upwardly from the leg to prevent the muscle from sliding off the leg.

A further object of this invention is to provide an ocular muscle hook that has a cylindrical handle combined with a configuration of handle, leg and tip to allow precise maneuverability of the muscle hook, to probe for the proper muscle, plow between that muscle and the schlera, and raise the muscle.

Other objects and advantages of the invention will be apparent from the description which follows.

SUMMARY OF THE INVENTION

This ocular muscle hook has a cylindrical handle similar in size, shape, weight, overall feel and maneuverability to a mechanical pencil. A shank projects from or is a continuation of the handle. A leg extends forwardly from the shank, but at an angle to the axis of the shank of approximately 120°. A tip is at an angle of about 150° from the leg, putting the tip at approximately a 90° angle to the axis of the handle. The shank is about $1\frac{1}{4}$ to $1\frac{1}{2}$ inches long and the leg is about $\frac{3}{8}$ to $\frac{1}{2}$ inch long. This form of muscle hook overcomes the problem of obstructing the view of the surgeon by the hand holding the muscle hook. The configuration of this muscle hook locates the holding hand laterally away from and out of interference with the surgeon's line of sight. The angulation of tip of the muscle hook, in projecting upwardly from the leg, prevents the eye muscle from sliding off the leg. The cylindrical handle affords comfort and flexibility of holding positions and allows precise maneuverability of the muscle hook through its various functions.

DESCRIPTION OF THE PREFERRED EMBODIMENT

Figure 1:
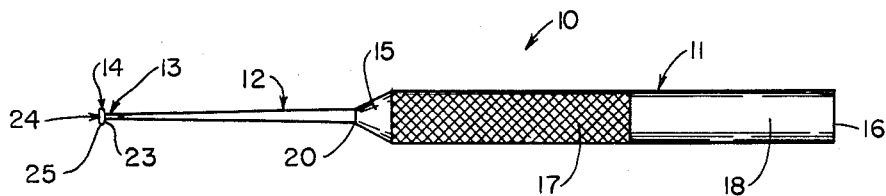
FIG. 1 is a top plan view of the ocular muscle hook.
Figure 2:
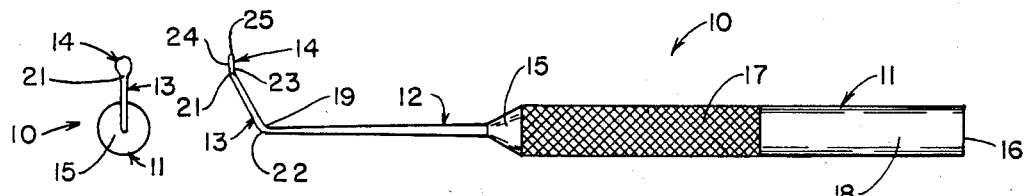
FIG. 2 is a side elevational view of the ocular muscle hook.
Figure 3:
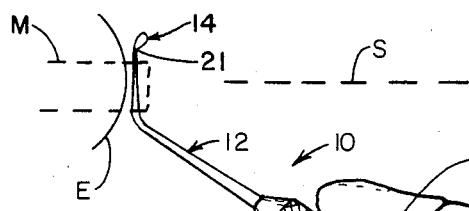
FIG. 3 is a front elevational view of the ocular muscle hook viewed from the left side of FIG. 2.

The primary components of this ocular muscle hook 10 are a body 11, a shank 12, a leg 13, and a tip 14 all preferably formed of stainless steel. The body 11 has a forward end 15 and a rearward end 16 and is substantially cylindrical in shape. A gripping section 17 on the body 11 is adjacent the forward end 16, and a rearward section 18 on the body is adjacent the rearward end 16. The gripping section 17 is preferably knurled.

The gripping section is about 2 inches long, whereas the overall length of the body 11 between the ends 15 and 16 is preferably about 3½ to 4 inches. The diameter of the body is about ⅜ inch. These dimensions allow the body to be held similarly to the way a pencil is held, as particularly illustrated in FIG. 4, with the gripping section 17 held between the thumb and fingers. The rearward section 18 may rest against the hypothenal space of the holder's hand H.

The shank 12 has a forward end 19 with a rearward end 20 adjoining and projecting forwardly of the forward end 15 of the body 11. The shank 12 is approximately 1⅜ inches in length for reasons which will be described hereinafter, and is relatively rigid.

The leg 13 has a forward end 21 and a rearward end 22. The rearward end 22 is joined to and extends from the forward end 19 of the shank 12. The leg 13 is approximately 7/16 inch long between the shank 12 and the tip 14. The angle defined by the shank 12 and the leg 13 is approximately 120°.

The tip 14 has a face 23 which is slighly convex and an upper heel or lower face 24 which is also slightly convex. The periphery 25 is preferably rounded. Thus, the entire tip 14 is free of any sharp edges. Also, the junction between the tip 14 and the leg 13 is somewhat rounded rather than being sharp. The diameter of the tip across the face 23 is about ⅛ inch. The plane of the tip 14 and the axis of the leg 13 define an angle of approximately 150°.

Figure 4:
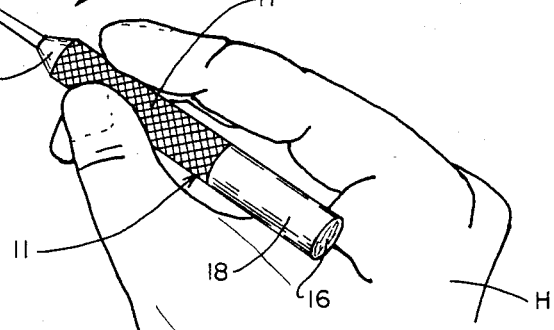
FIG. 4 is a diagramatic view showing the ocular muscle hook in use raising an eye muscle and showing the position of a surgeon's hand or an assistant's hand relative to the line of sight of the surgeon as he views the operating area.

In use, the ocular muscle hook 10 is held as illustrated in FIG. 4. The thumb and first two fingers hold the gripping section 17 between them.

To better appreciate the function of this muscle hook, it will help to describe briefly the relationship of the eye muscles to an eye. Movement of an eye is controlled by eye muscles attached to the eyeball. Strabismus is a condition of unbalanced muscular coordination of the eyes of an individual. One eye does not achieve binocular vision with the other because it deviates inward, outward, upward or downward. In ocular surgery to correct strabimus, an eye muscle M may need to be shortened or lengthened. The surgical procedure requires severing of the muscle M from the eyeball E and subsequent reattachment of the muscle. To give the surgeon clear access to that muscle M for cutting it, the muscle should be pulled or lifted away from the eyeball E so the surgeon can cut the muscle without damaging the eyeball. This lifting of the eye muscle is what the muscle hook of this invention does.

Initially, the tip 14 is utilized to probe for or identify the eye muscle that is to be cut. For this action, the tip is oriented approximately parallel to the surface of the eyeball E. This position of the tip is achieved by pivoting the body 11, a maneuver made easier by the cylindrical shape of the gripping section 17.

Figure 5:
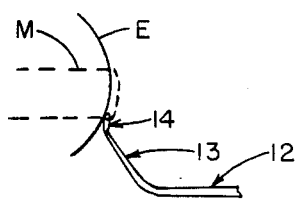
FIG. 5 is a partial diagramatic view showing the muscle hook in a probing position.

When the proper eye muscle has been identified and located, the tip 14 of the muscle hook 10 is slid behind the muscle M between the muscle and the eyeball E, as shown in FIG. 5. For initiation of this motion, the tip is held generally parallel to the surfaces of the muscle M are the eyeball E. Since the faces 23 and 24 of the tip and slightly convex and the periphery 25 is rounded, there are no sharp edges to cut or tear the schlera of the eye E or the muscle M.

After the initial penetration of the tip 14 under the muscle M, the muscle hook 10 is pushed and slightly pivoted to cause the tip to "plow" through the area between the eye muscle M and the schlera of the eye E. This "plowing" is continued until the tip 14 emerges beyond the other side of the eye muscle M. At this time the muscle hook 10 will have been gradually pivoted until the leg 13 is essentially parallel to the muscle M and the surface of the eyeball E.

The muscle hook 10 is now positioned to raise the eye muscle M. This movement is accomplished by the hand H in applying a lifting force to the body 11. Once lifted, the muscle hook 10 is held steady to keep the eye muscle M raised so it can be cut from the schlera by the surgeon. For this lifting and holding function of the hand H, the muscle hook is more comfortably and effectively held with the gripping section 17 between the thumb and fingers of the hand H and the rearward section 18 resting against the hypothenar space of the hand.

FIG. 4 illustrates the ocular muscle hook 10 being held in a surgeon's hand H (or the hand of a surgeon's assistant) with the leg 13 shown holding the eye muscle M away from an eyeball E. It may be noted that the approximately 7/16 inch length of the leg is greater than the width of an eye muscle which is normally about 8-9 mm. The dotted line S indicates the line of sight of the surgeon as he or she is performing the operation.

As can be seen from FIG. 4, the combination of the angles between the shank 12 and the leg 13, together with the length of the shank 12, cooperate to position the hand H away from the surgeon's line of sight S. Therefore, as the muscle hook 10 holds the muscle M, the surgeon can perform his operation with good visual contact with the area of operation. FIG. 4 also illustrates how the tip 14 and the shank 12 act as lateral stops at opposite ends of the leg 13 to keep the muscle M from sliding off the leg 13.

The foregoing has described an ocular muscle hook that fulfills the objects and advantages sought therefore. However, other modifications and variations are within the scope of the invention as set forth in the claims which follow.

What is claimed is:

1. An ocular muscle hook comprising an elongated handle assembly including a longitudinal axis, a forward end and a generally cylindrical handle portion extending rearwardly from said forward end, said handle portion having a generally cylindrical outer periphery;

a leg fixed to said forward end of said handle assembly and extending therefrom at a first obtuse angle in a first direction generally transversely of said longitudinal axis, said leg having an opposite free end; and a disk-like tip having a generally curved outer periphery fixed to said free end of said leg, said tip being sized and shaped to be inserted between an eye muscle and an eyeball and be pulled against the eye muscle without injury to the eye muscle or the eyeball, said tip extending from said free end of said leg at a second obtuse angle in said first direction transversely of said longitudinal axis substantially beyond said outer periphery of said handle portion whereby the user's hand may be positioned about said handle portion with said tip inserted under the eye muscle with the user's hand away from and not obstructing, the line of sight of a surgeon operating on the eye muscle and the eyeball.

2. The ocular muscle hook of claim 1 wherein said tip includes a longitudinal axis generally perpendicular to said longitudinal axis of said handle assembly.

3. The ocular muscle hook of claim 2 wherein said first obtuse angle is about 120° and said second obtuse angle is about 150°.

4. The ocular muscle hook of claim 3 wherein said handle assembly further includes an elongated shank fixed to said forward end of said handle portion, said shank having a diameter substantially smaller than the diameter of said handle portion, said shank further including a forward end, and a longitudinal axis coinciding with said longitudinal axis of said handle assembly, said leg being fixed to said forward end of said shank.

5. The ocular muscle hook of claim 4 wherein said disk-like tip includes smoothly curved, convex forward and rearward faces, said forward face being adapted to contact the eyeball without injury thereto and said rearward face adapted to contact the eye muscle without injury thereto.

6. The ocular muscle hook of claim 5 wherein said handle portion further includes a rearward end, said forward end of said handle portion having a knurled outer periphery, the length of the handle portion being such that when said knurled forward end is gripped between the fingers of a user, said rearward end rests against the base of the user's hand.

7. The ocular muscle hook of claim 6 wherein the handle portion is substantially longer than said shank, said shank is substantially longer than said leg, and said leg is substantially longer than said tip whereby the ocular muscle hook may be held in a vertical plane and the user's hand may be positioned away from, and not obstructing, the line of sight of a surgeon operating on the eye muscle and eyeball.

* * * * *